US00PP16056P3

(12) United States Plant Patent
White

(10) Patent No.: US PP16,056 P3
(45) Date of Patent: Oct. 25, 2005

(54) MINIATURE ROSE PLANT NAMED 'SAVADOUBLE'

(50) Latin Name: *Rosa chinensis hybrida*
Varietal Denomination: SAVadouble

(75) Inventor: Wendy R. White, Ipswich, MA (US)

(73) Assignee: Nor'East Miniature Roses, Arroyo Grande, CA (US)

( * ) Notice: Subject to any disclaimer, the term of this patent is extended or adjusted under 35 U.S.C. 154(b) by 138 days.

(21) Appl. No.: 10/404,763

(22) Filed: Mar. 31, 2003

(65) Prior Publication Data

US 2004/0194174 P1 Sep. 30, 2004

(51) Int. Cl.[7] ..... A01H 5/00
(52) U.S. Cl. ..... Plt./127
(58) Field of Search ..... Plt./101, 120, 136, Plt./127, 118, 119, 121

(56) References Cited

U.S. PATENT DOCUMENTS

| | | | | | |
|---|---|---|---|---|---|
| PP2,321 | P | * | 11/1963 | Boerner | Plt./141 |
| PP4,471 | P | * | 10/1979 | Saville | Plt./116 |
| PP6,568 | P | * | 1/1989 | Benardella | Plt./122 |
| PP6,859 | P | * | 6/1989 | Laver | Plt./119 |
| PP14,106 | P3 | * | 8/2003 | Kordes | Plt./119 |

* cited by examiner

*Primary Examiner*—Kent Bell
*Assistant Examiner*—W C Haas

(57) ABSTRACT

'SAVadouble' is a new and distinct variety of miniflora rose plant which, when grown under optimum conditions, may be identified by its large, hybrid tea form, golden-apricot colored flowers with a strong fragrance. The plant has an upright and spreading habit and is clothed in deep green glossy foliage.

1 Drawing Sheet

Genus/species: *Rosa chinensis hybrida.*
Varietal denomination: 'SAVadouble'.

CROSS REFERENCE

The present invention bares some resemblance to 'LAVjune' (U.S. Plant Pat. No. 6,859), which is one of the grandparents of this rose, having a similar plant habit and flowers of similar hybrid tea type form and being a similar golden yellow color.

This present invention also bares resemblance to 'SAVapeach' (U. S. Plant patent application Ser. No. 10/306,392, now abandoned) which is from this same breeding program. Both varieties are minifloras with fully double flowers, both varieties are notably fragrant and the coloring of their flowers is very similar, depending on temperature and plant nutrition. The relationship between 'SAVapeach' and this new invention is through the pollen parents. The pollen parent of 'SAVapeach ' is 'KORtember' (unpatented). The pollen parent of the new invention is 'BENday' (U.S. Plant Pat. No. 6,568) and the pollen parent of 'BENday' is also the 'KORtember'.

BACKGROUND OF THE INVENTION

This present invention relates to a new and distinct variety of hardy, bush type plant of the miniflora rose class. This new variety was created by me in a greenhouse in Rowley, Mass., by crossing the following two rose plants:

The seed parent is an unnamed, unintroduced, seedling of the miniature rose class with apricot colored flowers which was created by crossing 'LAVjune' (U.S. Plant Pat. No. 6,859) with an unnamed and unintroduced, orange-red, miniature seedling of 'Zorina' (U.S. Plant Pat. No. 2,321 by 'Baby Katie' (U.S. Plant Pat. No. 4,471.

The pollen parent is 'BENday' (U.S. Plant Pat. No. 6,568).

Two of the goals of this breeding program are fragrance and exhibition, hybrid tea type form. The seed and pollen parents are both fragrant and of exhibition, hybrid tea type form. The new variety is also fragrant with good exhibition, hybrid tea type form. In this regard, this was a successful cross.

Differences between this new invention and both its pollen and seed parent are that the flowers of this new invention are a novel color and are larger and with a higher petal count. Flowers of the new invention have 28 to 36 petals and are a golden-yellow. The pollen parent has 23 to 25 petals and cardinal red flowers with the only yellow being towards the base of its petals. The seed parent's flowers have 17 to 22 petals and are an apricot and yellow blend, apricot being the predominant color.

Asexual reproduction by cuttings of this new variety in Rowley, Mass. shows that all distinguishing characteristics of this rose continually come true to form.

SUMMARY OF THE INVENTION

The present invention relates to a new and distinct variety of hardy dwarf bush type rose plant of the miniflora class; the variety being primarily characterized—as to novelty—by it's hybrid tea-form, golden-yellow blooms large in size, qualifying it for the miniflora class, and its strong fragrance. One unique characteristic possessed by this new variety which distinguishes it from other varieties of which I am aware is the strikingly different color and form of the bloom as growing conditions decline from ideal. The coloring and form of the flowers of this new variety are very dependent on the pH of the soil and proper nutrition. The color lightens respectively and the length of the inner petals becomes shorter as its growing media becomes more acid and nutrients become less available to the plant. While the flower is still attractive and fragrant, it no longer attains its high-centered, hybrid tea like form. With the addition of lime and the necessary nutrition the plant recovers rather quickly and new flowers again have the deeper coloring and hybrid tea type form.

Other notable characteristics are:

An abundance of flowers borne mostly solitary but also in small pyramidal clusters, usually of 3 or 4

Glossy, dark green foliage

A plant which is very well branched

A plant which grows quite satisfactorily in large containers and is good for cut flowers and exhibition.

BRIEF DESCRIPTION OF THE DRAWING

The accompanying color photograph shows specimens of this new variety in different stages of development as grown under plastic in February and March in Essex County, Mass., and showing the different golden shades which the flowers may be.

BOTANICAL DESCRIPTION OF THE PLANT

Following is a detailed description in outline form pertaining specifically to this new and distinct variety of miniature rose plant as observed at 5 years of age, growing indoors, under plastic in Essex County, Mass. All major color plate identifications made are referring to The Royal Horticulture Society Colour Chart except where common terms of color definition are employed.

Genus/species: *Rosa chinensis hybrida.*
Varietal denomination: 'SAVadouble'.
Commercial class: Miniflora rose.
Seed parent: ('Zorina' by 'Baby Katie') by 'LAVjune'.
Pollen parent: 'BENday'.

FLOWERS

Blooming habit: Recurrent.

Borne: Mostly solitary but also in small pyramidal clusters of 3 or 4 with the terminal bud opening and fading before the rest of the buds in that same cluster begin to unfurl.

Bud:

*Size.*—13/16 inch to one inch long just before the sepals divide, and having a diameter of ½ inch at the widest point.

*Form.*—Tapered, obovate with an acute tip.

*Sepals.*—Color — olive green, near 144A with near 145A in the center and towards the base; inner surface is lighter, near 147C with near 145C in the center and towards the base. Appearance — inside surface is lightly pubescent and outside surfaces are glaborous except for a few (between 3 and 9) hairs right on the midrib. Size — the three innermost sepals are 15/16 to 1⅛ inches long and ¼ inch wide; the two outer sepals vary greatly in length from 1 to 1½ inches but remaining narrow at about ¼ inch wide, excluding appendages. Characteristics — extending ⅜ to ½ inch beyond the tip of the bud just before they start to divide; lanceolate; margins of the 2 innermost sepals are ciliate with a few stipitate glands; margins of the 2 outermost sepals have many hairs and many stipitate glands and 0 to 2 foliacious appendages along one or both edges and the appendages also have ciliate margins and 2 or 3 stipitate glands on each margin; and one sepal between the 2 inner and 2 outer sepals usually having the traits of both the inner and the outer sepals at the same time resulting in each of its margins being different. As the flower opens the sepals roll back toward the stem and eventually rolling back to the stem.

*Peduncle:*

*Length.*—Usually 1 to 1⅜ inches.

*Aspect.*—Straight.

*Strength.*—Strong, erect.

*Color.*—Yellow green, near 146B.

*Texture.*—Glabrous and may have a few glands or no glands but sometimes having a dozen or more stipitate glands.

Receptacle:

*Diameter,*—9/32 to 10/32 inch.

*Color.*—Near 144A.

*Texture.*—Glabrous.

Bloom:

*Size.*—When fully expanded — 2½ to 3¼ inches.

*Form.*—From when the petals start to unfurl and right to petal drop the profile of the bloom always is flat across the top; at the same time the lower profile progresses from narrow cupped to broad cupped as the petals roll back and finally to flat when full open; outer petal edges reflex slightly as they open giving a ruffled appearance from the top view, reflexing of the petals intensifies as the bloom matures, sometimes to the point of being quilled.

*Petalage.*—28 to 36.

*Petaloids.*—3 to 9 in the spring, 13 or up to 17 in the fall.

*Fragrance.*—Strong, sweet rose.

*Persistence.*—Usually drops off cleanly in 8 to 12 days.

*Lasting quality as cut flower.*—5 to 8 days.

Petals:

*Texture.*—Glaborous.

*Appearance.*—Inside — velvety, outside — satiny.

*Form.*—The outermost petals are very broad fan shaped, tapering toward the bottom and with an obovate lower margin with a pedestal-shaped base at its center that attaches the entire petal to the receptacle, and having a crescent shaped outer edge and usually having a single serration at the apex; progressing toward the center of the bloom the shape of the petals gradually changes from broad fan shaped to obovate with the outer edge being rounded and slightly emarginate near the apex and occasionally having a single serration at the apex and a more pronounced pedestal-shaped base.

*Size.*—Outer petals — 15/16 inch to 1⅛ inches wide tapering to around ½ inch wide and the pedestal base of 4/32 to 5/32 inch wide and near 1/16 inch long or less; innermost petals may be as narrow as ½ inch wide but still near the same length as the outer petals, 1 1/16 to 1⅛ inch, and the pedestal base is 4/32 inch wide and usually 1/16 inch in length.

*Arrangement.*—Overlapping but not evenly spaced.

*Petaloids.*—Ruffled appearance with emarginate edges, tapering from 3/32 to 2/32 inch at the point of attachment and having a pedestal base up to 3/16 inch long; occasional petaloids are attached to filaments instead of a pedestal-shaped base.

*Color.*—A low soil pH and lack of nutrient availability can cause the flowers to be near white, as a color between 158C and 11D, from bud stage right through to faded bloom. Also noteworthy is the fact that the bud and newly opened blooms may start off as different colors even on the same plant but all seem to fade to the same or similar soft gold. The following colors were taken from plants with near optimum nutrient availability. Generally, petals are varying shades of pinks and oranges with varying bright shades of yellow near the base. Color when sepals first divide — most often between 25C, nasturtium orange and 23C, cadmium orange. During the first few days — inside of the inner petals is near 25C, nasturtium orange with outer edges between 25C and 23C, and maize yellow, near 21B, near the base; reverse is near 23D, cadmium orange for the upper two thirds and blending into saffron yellow, near 21C, at the base. Inside of the outer petals is near 28C blending into 21B from the base, and the reverse is tangerine orange, near 24C, blending into near 21C from the base. After three or more days — outer petals becoming entirely salmon, near 27A, and inner petals becoming between 29C, carrot red, and 32D, Chinese coral, and the yellow portion of the petals lightening a little to a straw yellow, near 13C. At this point, the petaloids are jasper red, near 39C, on the upper portion and straw yellow, near 13C, on their lower portion and up through the centers. The reverse of the inner and outer petals is near 29C for the top third and then blending into a medium yellow, near 12C; the reverse of the petaloids is chrome yellow, near 15D, on the upper half and blending quickly into a medium yellow, near 12C on lower half.

When buds start out a softer apricot the following is the coloring that will be observed:

*When sepals first divide.*—Between 29D, peach, and 36A, orient pink during the first few days — outer petals, upper surface — may have a pink tone of near 36A, becoming shell pink, near 37C, as it progresses down the petal and as the color combines with a bright lemon yellow, near 13B, which is coming up from the base; the inner petals, upper surface — is near 37C, becoming near 33D, shrimp red, as it combines with the yellow. The petaloids are between 33D and 37A on their upper ⅔s to ¾s and then blending into near 13B towards the base; the reverse of the outer petals is an orient pink, near 36C, for the upper third and combining with near 8C, mimosa yellow, from the lower third to become near 19D, Egyptian buff, for the middle third, and being chartreuse green, near 154B, near the point of attachment; the reverse of the inner petals is a shell pink, near 37C, around the upper edge, Indian yellow, near 17D for most of the reverse and near 2C, light chartreuse yellow, around the point of attachment; the reverse of the petaloides is again more intense being a pink near 37B for the upper third and the remainder being near 17D.

When buds start out a plain yellow the following is the coloring that will be observed:

*When sepals first divide.*—Near 19A, from the orange-yellow group during the first few days — outside of outer petals is a medium yellow, near 19A becoming salmon, near 27B, along the edges and a lemon yellow, between 13C and 14B, near the base; inside of outer petals is a chrome yellow, near 15C, up from the base and becoming salmon, near 27B, along the edges; inside of inner petals is a marigold orange, near 28C, with buttercup yellow, near 15B, up from the base; outside of inner petals is near 28D and near 27A along the edges and lemon yellow, near 14C near the base.

As the bloom ages it gradually lightens, loosing its pink tonality which gave it its apricot or gold coloring before the petals drop, finally becoming a pale salmon pink, near 27D, on the outer half of the outer petals and blending into a light barium yellow, near 10A, towards the base and a medium aureolin yellow, near 12B, at the point of attachment; inner petals are near 27C on the outer two thirds, blending into near 10B, barium yellow, towards the base and 12B at the point of attachment; reverse of outer petals is near 27D for the upper half and blending into near 10C and near 10B at the point of attachment; the reverse of the inner petals is near 27D for the upper two thirds, blending into near 10D and near 10B at the point of attachment.

Regardless of the color it starts as, the colors continue to lighten slightly and fade: the entire upper surface of inner and outer petals being varying shades between 27C, a salmon pink, and 20C, a Chinese pink, and petaloides being near 36B, orient pink, on both surfaces and all being a light yellow, near 13D, at the base.

*General tonality.*—Golden-apricot.

Petaloids:

*Size.*—Width — ¾ inch at the widest point. Length — quite variable from ¼ inch to 7/16 inch.

*Form.*—Quite emarginate and loosely contorted but always narrower at the base.

REPRODUCTIVE ORGANS

Stamens, filaments and anthers:

*Arrangement.*—Attached at the outer rim of the receptacle.

*Quantity.*—75 to 85.

*Filaments.*—Length — varying 3/26 to 6/16 inch. Color — near 160A from the greyed-yellow group.

*Anthers.*—Color — medium yellow, near 12C.

*Pollen.*—Color — near 162A from the greyed-orange group.

*Quantity.*—Moderate amount.

Pistils, styles and stigmas:

*Quantity.*—About half as many as stamens, around 40.

*Styles.*—Thin, undulating; uneven length, 4/32 to 9/32 inch. Color — translucent, yellow-green near 153C.

*Stigmas.*—Color — a shade lighter than the styles, near 153D.

Hips: Does not readily self-pollinate but will accept some pollens using normal hybridizing procedures.

*Shape.*—Pumpkin seed shaped, seeds do not protrude.

*Size.*—Usually 11/16 inch in diameter.

*Color.*—Becoming near 169B from the grayed-orange group.

*Seed color.*—A light "grayed" yellow, between 162C and 162D.

PLANT

Habit: Upright and well branched.

Growth: Vigorous and uniformly branched, maturing at a height between 26 and 30 inches and a width of about 2 feet.

Length of flowering stem: Averaging 6 inches when borne singly.

Foliage: Pinnately compound with 7 leaflets, occasionally with 3 or 5 leaflets; anthocyanin reddish-purple coloring present on young growth.

*Size of mature leaf.*—3½ inches from point of attachment to tip when measured along the rachis. Mature terminal leaflet — 1 7/16 inches from base to tip and ⅞ to 1 inch in width at the widest part. Mature basal leaflet — ⅞ to 1 inch in length from base to tip and 9/16 to 10/16 inch wide at the widest part.

*Quantity.*—Abundant.

*Leaflets.*—Shape — ovate, acute apex; terminal leaflet has rounded base, side leaflets are unevenly attached to the petiolule by as much as 1/32 inch. Color — new foliage — upper surface, medium dark green, between 146A and 147A, flushed lightly with near 183C, under surface between 147B and 147C, flushed with near 183C; older foliage — very dark green, between 139A and 147A, on the upper surface and a medium green, near 147B, on the reverse. Appearance — glossy on the upper surface and matte on the underside, veins visible and being slightly lightly lighter than the leaflet except the main vein which is lighter, near 146D. Texture — upper surface is smooth and glabrous under surface is glabrous and leathery Margin — fine to somewhat coarse and uneven serration with glands on the tips of the serration and with stipitate glands at the tip of and occasionally on the side of the serration near the base of the leaflets.

*Rachis/petiole.*—Color on young leaf — upper side is a deep reddish purple, near 187A, along the ridge and the groove is flushed heavily with near 184C; underside near 146D flushed with near 183C down to where the stipules are attached and then is near 146C with no anthocyanin coloration; color on old leaf — upper side has ridges of dark green, near 147A, along side a medium green groove of near 147D and the groove becoming lighter, near 145C from the basal leaflets to attachment at the plant stem; the underside light green, near 146D at its base and becoming near 147C near the terminal leaflet. Texture — upper side may have occasional fine hairs in the groove with clusters of short and fine hairs at the point of attachment of the petiolules; there are stipitate glands along each ridge of the groove and opposite or nearly opposites those on the facing ridge; underside is glabrous with 3 to 5 prickles on the mature leaf. Length — 2⅛ to 2½ inch from attachment at stem to base of terminal leaflet.

*Petiolules.*—Color on both young and mature growth is the same as that of the rachis. Appearance — there are stipitate glands along the ridges of the upper surface and occasionally a cluster of 2 or 3 near the point of attachment to the petiole and there is apt to be a single hair where it attaches to the petiole on both upper and under surfaces. Length — usually 1/16 inch on young foliage and 2/16 inch on older foliage.

*Stipules.*—Margin is usually tightly reflexed, is coarsely and very unevenly serrated with glands on the tip of each serration and stipitate glands between and on the sides of the serration. Size — about 3/16 inch wide tapering to 1/16 inch wide at the base of the leaf and varying from 5/16 to 7/16 inch in length. Color — on young leaf — upper surface near 146C flushed very lightly with near 187A, under side near 146D flushed very lightly with near 183C; on mature leaf — upper surface between 137B and 147B, underside is near 137C.

Resistance: Good resistance to downy and powdery mildews and insects; average resistance to blackspot; no rust observed.

Wood:

*New wood.*—Texture — glabrous. Color — between 137B and 147B.

*Old wood.*—Texture — glabrous but with numerous small thorns. Color — near 137C.

Thorns: Quantity on main stalks — 10 to 14 thorns per inch; on laterals — 3 to 6 per inch.

*Form.*—Elliptical base, straight, accuminate being 3/16 to 6/16 inch in length.

*Color when young.*—The two thirds closest to the stem are a soft salmon pink, near 185A from the red-purple group, and the very tips are a light green, near 147C (With lower nutrition young thorns may be considerably lighter, near 182C, and the tips are near 147D).

*Color when old.*—Near 176A from the greyed-orange group.

*Prickles.*—Found on underside of rachis, near 146D flushed with near 183C.

Stipitate glands: Are usually a color near 183C.

Winter hardiness: Hardiness has only been tested in zones 6 and 9 with ample winter protection recommended zones 7 and colder.

It is claimed:

1. A new and distinct variety of hardy miniflora rose plant is claimed, substantially as illustrated and described, the variety being primarily characterized—as to novelty—by it's apricot- or golden-yellow blooms with strong fragrance and a well branched plant having dark green glossy foliage.

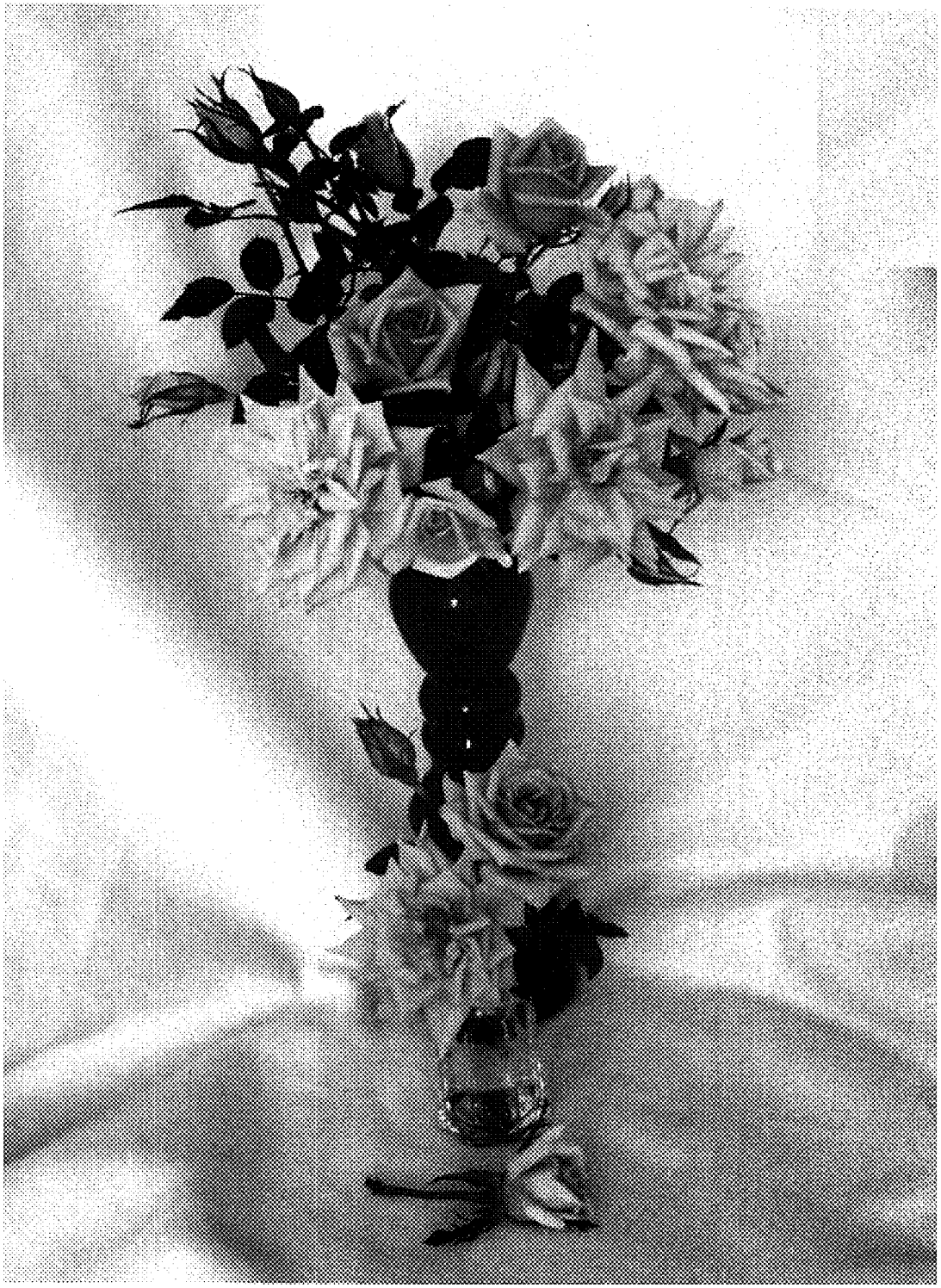

* * * * *